United States Patent [19]

Piechota, Jr.

[11] Patent Number: 4,647,451

[45] Date of Patent: * Mar. 3, 1987

[54] ANHYDROUS DENTIFRICE

[75] Inventor: Stanley E. Piechota, Jr., Somerset, N.J.

[73] Assignee: Colgate-Palmolive Company, New York, N.Y.

[*] Notice: The portion of the term of this patent subsequent to Apr. 15, 2003 has been disclaimed.

[21] Appl. No.: 822,518

[22] Filed: Jan. 27, 1986

Related U.S. Application Data

[62] Division of Ser. No. 609,261, May 11, 1984, Pat. No. 4,582,701.

[51] Int. Cl.$^4$ .......................... A61K 7/16; A61K 7/18
[52] U.S. Cl. ........................................ 424/52; 424/49; 424/57; 424/151
[58] Field of Search ...................... 424/49, 52, 57, 151

[56] References Cited

U.S. PATENT DOCUMENTS

| | | | |
|---|---|---|---|
| 4,132,771 | 7/1979 | Schreiber et al. | 424/49 |
| 4,159,316 | 6/1979 | Januszewski et al. | 424/49 |
| 4,582,701 | 4/1986 | Piechota, Jr. | 424/52 |

Primary Examiner—Donald B. Moyer
Assistant Examiner—F. T. Moezie
Attorney, Agent, or Firm—Robert L. Stone; Murray M. Grill; Herbert S. Sylvester

[57] ABSTRACT

Anhydrous dentifrice having desirable rheological, sensory and hygienic characteristics containing a polysaccharide gum and glycerine humectant. Ingredients at least partially incompatible when water is present, such as zeolite or molecular sieve, may be included. The polysaccharide is clarified or non-clarified deacetylated heteropolysaccharide S-60.

6 Claims, No Drawings

ANHYDROUS DENTIFRICE

This is a division of application Ser. No. 609,261, filed May 11, 1984, now U.S. Pat. No. 4,582,701.

This invention relates to an anhydrous dentifrice having desirable rheological, sensory and hygienic characteristics.

Dentifrices typically contain assorted ingredients dispersed in a creamy or gel vehicle, which vehicle contains a liquid phase and solid phase. The literature often indicates that the liquid phase may be water, humectant or mixture thereof. In point of fact, water is generally present since it is difficult to formulate an anhydrous dentifrice containing humectant as vehicle liquid phase component with many of gum or gum-like gelling materials recognized in the art as solid phase vehicle components with desirable cream or gel consistency without sacrificing rheological, sensory and/or hygienic characteristics. Gelling materials which provide desirable consistency with water and humectant are often less satisfactory when water is not present to activate their gellation binding properties. This is particularly a problem when glycerine is used as humectant, even though glycerine is the most commonly used humectant in water-containing dentifrices.

Nevertheless, anhydrous dentifrices have been proposed since various ingredients helpful in providing effects sought from a dentifrice are not compatible with water and have such effects diminished or lost. For instance, anhydrous zeolite or molecular sieve material produce warming heat when moistened by saliva upon introduction into the oral cavity, which effect is not provided with aqueous dentifrice. Similarly, soluble fluorine retention may be less than optimum when water and calcium or magnesium ions are present or sodium bicarbonate, or other ingredients, such as the sweetening agent N-levo-alpha-aspartyl-levophenylaniline-1-methyl ester, also known as aspartame are present, which ingredients are inactivated completely or partially in the presence of water.

U.S. Pat. No. 3,250,680 to Menkart et al discloses a heat-generating cosmetic composition adapted to evolve heat when it contacts moisture which is an anhydrous composition containing about 5 to 40% of an anhydrous adsorbent material such as an alkali metal aluminosilicate molecular sieves dispersed in a non-aqueous cosmetically acceptable vehicle such as mineral oil or liquid polyalkylene glycol. The cosmetic compositions disclosed herein include skin and hand creams, shampoos and toothpaste. The anhydrous toothpaste formula therein does not contain glycerine.

U.S. Pat. No. 3,574,824 to Echenandia et al discloses an anhydrous toothpaste formulation which does not generate heat during brushing comprising an oil, a combination of polyethylene glycols, a non-ionic emulsifier, a binding agent, a compound having a negative heat of hydration such as mannitol or inositol, and 30–70% abrasive which may be aluminum hydrate and/or calcium sulfate and aluminum silicate. There is no zeolite present in these formulations and they do not release or generate heat as do those of U.S. Pat. No. 3,250,680. Bleaching agents and fluorides are among the materials disclosed which may be present even though they would exhibit incompatibilities if water were present.

U.S. Pat. Nos. 4,132,771 and 4,187,287, each to Schreiber et al describe heat-generating anhydrous dentifrice containing zeolite and flavoring agent. U.S. Pat. No. 4,159,316 to Januszewski et al describes anhydrous self-heating dentifrice containing zeolite in which the liquid phase of the vehicle is propylene glycol and the solid phase is hydroxypropyl cellulose. Zeolite NaHA in dentifrices is described in U.S. Pat. No. 4,349,533 to Dent et al.

It is an advantage of this invention that desirable rheological, sensory and hygienic characteristics are attained in an anhydrous dentifrice containing an ingredient which would be at least partially incompatible with water.

It is a further advantage of this invention that an anhydrous dentifrice with a rigid gel consistency is provided with a polysaccharide gum as binding agent with glycerine as humectant.

Further advantages of the invention will be apparent from consideration of the following specification.

In accordance with certain of its aspects, the present invention relates to an anhydrous dentifrice comprising at least about 50% by weight of glycerine humectant and at least about 0.1% by weight of deacetylated heteropolysaccharide S-60 to provide a rigid gel consistency to said dentifrice.

In the prior art, glycerine has generally been avoided as humectant in anhydrous dentifrice. In U.S. Pat. No. 4,159,316 to Januszewski et al, it is described with regard to Table 2 thereof that when a zeolite material is added to glycerine, heat is evolved too early to permit a dentifrice user to sense the heat when the dentifrice is anhydrous. In the present invention in which the deacetylated heteropolysaccharide S-60 is used as gelling agent with glycerine, the early evolution of heat upon addition of anhydrous zeolite material is not experienced and heat is first evolved when the anhydrous dentifrice is moistened by saliva during use.

It is understood that glycerine as commercially available may contain about 0.5–2% by weight of water in association with the glycerine, typically about 0.7%. The presence of such minor amount of water does not prevent the dentifrice from being considered by the artisan as anhydrous.

Glycerine is present in the anhydrous dentifrice in amount of at least about 50% by weight, typically about 50–80% by weight, preferably about 65–75%. It is generally about 90–100% by weight of the liquid phase of the anhydrous dentifrice. If desired, a minor amount of additional non-aqueous liquid, such as polyethylene glycol having an average molecular weight of about 200–600 or propylene glycol may be present to assist dispersion. Polyethylene glycl 600 is preferred. It is noted that in dentifrices in general, these type of materials also reduce the tendency of the dentifrice to form a string when extruded. In the dentifrices of the present invention there is little, if any, string formed even if the dispersing agent is not present. Such additive is typically present in amount of about 1–5% by weight of the anhydrous dentifrice and up to about 10% by weight of the amount of glycerine.

The formation of heteropolysaccharide S-60 by fermentation of *Pseudomonas elodea* and deacetylation is described in each of U.S. Pat. No. 4,326,052 to Kang et al and U.S. Pat. No. 4,326,053 to Kang et al, the disclosures of which are incorporated herein by reference. In U.S. Pat. No. 4,326,052, non-clarified and clarified variants of deacetylated heteropolysaccharide S-60 are described. In the non-clarified form about half of the material is insoluble of which about 34% (wt./wt.) is protein. In the clarified form, no more than 2% by weight of the total materials is protein. Heteropolysaccharide S-60 and its deacetylated forms are available from Kelco Division of Merck and Company, San Diego, Calif.

Deacetylated non-clarified heteropolysaccharide S-60 comprises (a) about 50% (wt.wt.) insoluble material of which about 34% (wt./wt.) is protein, and (b) about 50% (wt./wt.) carbohydrate which contains abut 22-26% (wt./wt.) glucuronic acid, 0% acetyl groups, and the neutral sugars rhamnose and glucose in the approximate molar ratio 3:2, said rhamnose and glucose sugars being primarily 1,4 β-linked, said heteropolysaccharide being further characterized in that it is anionic, and forms brittle, thermoreversible gels.

Deacetylated clarified heteropolysaccharide S-60 comprises no more than about 2% (wt./wt.) protein and carbohydrate said carohydrate containing about 22-26% (wt./wt.) glucorinic acid, 0% acetyl groups, and the neutral sugars rhamnos and glucose inthe approximate molar ratio 3:2, said rhamnose and glucose sugars being primarily 1,4 β-linked, said heteropolysaccharide being further characterized in that it is anionic, and forms brittle, thermoreversible gels.

The deacetylated heteropolysaccharide in amount of at least about 0.1-5% by weight, preferably about 0.3-1% and most preferably about 0.3-0.5%, of the anhydrous dentifrice is mixed with glycerine by conventional dentifrice hot-processing technique at about 65°-95° C. and cooled. During cooling the gel mass breaks into portions which over a period of time loosely adhere to adjacent portions. This characteristic results in an anhydrous dentifrice in which dentifrice extruded out of a dentifrice tube rheologically cleanly and evenly and readily separates from the dentifrice still inside the tube without formation of a string.

Clarified deacetylated heteropolysaccharide is preferred for use when a substantially white dentifrice or visually clear gel dentifrice is desired. The whiteness may be increased with a pigment such as titanium dioxide.

Molecular sieves such as synthetic zeolites, particularly A crystals and X crystals, have been disclosed as dentifrice abrasives or polishing agents in anhydrous dentifrices, for instance in U.S. Pat. Nos. 4,132,771 and 4,187,287, each to Schreiber et al, in U.S. Pat. No. 4,159,316 to Januszewski et al, the disclosures of which are incorporated by reference. pH adjusted zeolite as dentifrice abrasive is described in U.S. Pat. No. 4,349,533 to Dent et al, the disclosure of which is incorporated by reference. Molecular sieves are also disclosed in U.S. Pat. No. 3,250,680 to Menkart et al, the disclosure of which is also incorporated herein by reference. In properly formulated anhydrous dentifrices, heat formation occurs when the molecular sieves come in contact with saliva upon introduction of the dentifrice into the oral cavity. The practice of the present invention with polysaccharide gum permits such an effect to occur in anhydrous dentifrice containing glycerine humectant.

Depending on the types of fluorine-providing material and insoluble polishing material which may be employed in an aqueous dentifrice, the retention of soluble fluorine can be substantially diminshed or eliminated by precipitation. In the anhydrous dentifrice of the present invention, combinations of fluorine-providing material and polishing agent which would be incompatible in the presence of water, can be employed with substantially optimum soluble fluorine retention.

Likewise, other agents which provide desirable effects, such as peroxide bleaching compounds which evolve oxygen and bicarbonate compounds, including sodium bicarbonate polishing agent, which evolve carbon dioxide can be readily formulated in the anhydrous dentifrice of the present invention.

Anhydrous zeolites or molecular sieves may be employed in amount of about 1-50% by weight of dentifrices, bicarbonates, such as sodium bicarbonate, in amount of about 1-50% fluorine-providing compounds, such as sodium fluoride, stannous fluoride or sodium monofluorophosphate and bleaching peroxygen bleaching compounds, in amounts to provide about 0.1-1% by weight of fluorine or oxygen; coumarin optical brighteners such as 4-methyl-7-hydroxy-coumarin and 4-methyl-1,7-diethylamino-coumarin would generally be present in amount of about 0.01-0.1% by weight and the sweetening agent aspartame would generally be present in amount of about 0.05-1% by weight.

Bleaching agents for the teeth, such as oxidizing agents, optical brighteners, and other such agents which achieve a whitening or brightening effect when applied to the teeth, may be added to our anhydrous toothpaste base. Sodium perborate, sodium pyrophosphate peroxide, hydrogen peroxide, sodium peroxide, sodium persulfate, sodium percarbonate, potassium peroxydiphosphate, and urea peroxide, added at levels of from about 0.1% to about 5%, preferably from about 0.5% to about 1% by weight, based on the finished toothpaste are especially recommended. They may be used alone or in combination with one another.

When the anhydrous dentifrice of the present invention contains fluorine-providing compound, fluorine provision is optimum even if there is also present a source of calcium or magnesium such as calcium chloride or magnesium chloride which may be present in amount of about 0.01-1% by weight of a polishing agent such as dicalcium phosphate, tri-magnesium phosphate, calcium carbonate, magnesium carbonate or the like, which could result in formation of calcium fluoride if water were present.

As mentioned earlier, polishing agent or abrasive in the anhydrous dentifrice of the present invention may be an anhydrous zeolite or molecular sieve, which causes generation of heat when moistened by saliva during use, or aluminum hydrate, (e.g. alpha-alumina hydrate or anhydrous alumina) calcium sulfate or aluminum silicate, such as are disclosed in U.S. Pat. No. 3,574,824. In addition, the polishing agent or abrasive could be from amongst the dentally acceptable materials typically used in the prior art, such as dicalcium phosphate, tricalcium phosphate, insoluble sodium metaphosphate, silica xerogel, sodium aluminosilicate (also characterized as silica containing combined alumina), magnesium carbonate, calcium carbonate, calcium pyrophosphate, bentonite, sodium bicarbonate and mixtures thereof. In particular, when the polishing agent or abrasive would be capable of providng alkaline earth metal ion (calcium or magnesium), which could form a precipitate of inactive calcium fluoride if a fluorine-providing material is present, the anhydrous medium of the present invention avoids such problem and permits optimum compatibility between polishing agent or abrasive and fluorine-providing material. Polishing material or abrasive is typically present in amount of about 5-50% by weight of the dentifrice. Anhydrous zeolite or molecular sieve, when present, is in amount of about 1-50% by weight.

The listing of polishing agent in the present specification is not intended to be exhaustive and therefore, for other polishing materials, reference should be made to a standard handbook, such as Cosmetics Science and Technology, by Sagarin, 2nd printing, 1963, published by Interscience Publishers, Inc.

The dentifrice of the present invention may optionally contain a fluorine-containing compound having a beneficial effect on the care and hygiene of the oral cavity, e.g. diminution of enamel solubility in acid and protection of teeth, against decay. Examples thereof include sodium fluoride, stannous and manganese fluoride, potassium fluoride, potassium stannous fluoride ($SnF_2 \cdot KF$), sodium hexafluorostannate, stannous chlorofluoride, sodium or potassium fluorozirconate and sodium monofluorophosphate. These materials, which dissociate or release fluorine-containing ions in water or saliva suitably may be present in an effective but non-toxic amount upon contact with water or saliva, usually within the range of about 0.01 to 1% by weight of water soluble fluorine content to the dentifrice. Sodium fluoride, stannous fluoride and sodium monofluorophosphate are preferred.

Organic surface-active agents are used in the compositions of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitably such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds in the dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particular suitable surface-active materials include nonionic agents such as condensates of sorbitan monostearate with approximately 20 moles of ethylene oxide, condensates of ethylene oxide with propylene oxide, ("Pluronic" materials) and amphoteric agents such as long chain (alkyl) amido-alkylene alkylated amine derivatives which are available under the trademark "Miranol" such as Miranol $C_2M$.

Other suitable nonionic detergents are the condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an α-olefin oxide to polyhydric alcohol mole ratio in the range of about 1:1 to 1:3. There may also be employed olefin sulfonate detergents, typically long chain alkenyl sulfonates.

It is preferred to use from about 0.05 to 5% by weight and preferably about 0.5 to 5% of the foregoing surface-active materials in the instant oral preparations.

Various other compatible and suitable materials may be incorporated in the dentifrice formulations of this invention. Examples thereof are coloring or whitening agents or dyestuffs, preservatives, silicones, chlorophyll compounds, ammoniated materials such as urea, diammonium phosphate, pH adjusting materials such as monosodium phosphate and mixtures, thereof, and other constituents. These adjuvants are incorporated in the instant compositions in amounts which do not substantially adversely affect the properties and characteristics desired and are selected and used in proper amount depending upon the particular type of preparation involved.

Synthetic finely divided pyrogenic silica such as those sold under the trademark Cab-O-Sil M-5, Syloid 244, Syloid 266 and Aerosil D-200 may also be employed in amounts of about 1-5% by weight to promote thickening.

Antibacterial agents may also be employed in the oral preparation of the instant invention to provide a total content of such agents of up to about 5% by weight, preferably about 0.01 to 5.0%, most preferably about 0.5 to 1.0%. Typical antibacterial agents include:

$N^1$-(4-chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1-(lauryldimethylammonium)-8-(p-chlorobenzyl-dimethylammonium)octane dichloride;
5,6-dichloro-2-guanidinobenzimidazole;
$N^1$-p-chlorophenyl-$N^5$-laurylbiguanide;
1,6-di-p-chlorophenyl biguanidohexane;
1,6-bis(2-ethylehexyl biguanido) hexane;
5-amino-1,3-bis(2-ethylhexyl)-5-methylhexahydropyrimidine; and other non-toxic acid addition salts.

Any suitable flavoring or sweetening sialagogues or mixture thereof may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange, as well as flavoring aldehydes, esters such as methyl salicycate, alcohols, and higher fatty compounds known in the art. Also useful are such chemicals as menthol, carvone and anethole. Of these, the most commonly employed are the oils of peppermint, spearmint and eucalyptus, and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if do desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, aspartame, the dipeptides of U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

The following Examples are given to illustrate this invention further. In this application all proportions are by weight unless indicated.

EXAMPLE 1

The following stable anhydrous dentifrice is prepared by the hot process technique at 85° C.

|  | PARTS |
|---|---|
| Glycerine (99.3%) | 70.49 |
| Polyethylene glycol 600[1] | 3.00 |
| Clarified deacetylated heteropolysaccharide S-60[2] | 0.30 |
| Silica containing combined 1% alumina[3] | 18.00 |
| Silica aerogel[4] | 5.00 |
| Titanium dioxide | 0.40 |
| Sodium monofluorophosphate | 0.76 |
| Flavor | 0.65 |
| Sodium saccharin | 0.20 |
| Sodium lauryl sulfate | 1.20 |

[1]Available from Union Carbide as Carbowax 600.
[2]Available from Kelco Division of Merck as Gelrite.
[3]Available from J.M. Huber as Zeo 49B.
[4]Available from Davison Division of Grace Inc. as Syloid 244.

The heteropolysaccharide forms a brittle clear gel in the hot process technique with glycerine. The dentifrice is introduced into a dentifrice tube and is extruded therefrom as a ribbon which readily and cleanly separates from dentifrice still in the tube when extrusion pressure is released.

When clarified deacetylated S-60 is replaced by non-clarified deacetylated S-60, the rheology is similar and the dentifrice color is yellow-white.

EXAMPLE 2

The following stable anhydrous heat-generating dentifrices are prepared by hot-processing at 85° C.

|  | PARTS | | |
|---|---|---|---|
|  | A | B | C |
| Glycerine (99.3%) | 72.75 | 68.30 | 68.40 |
| Polyethylene glycol 600[1] |  | 3.00 | 3.00 |
| Clarified deacetylated heteropolysaccharide S-60[2] | 0.30 | 0.40 | 0.40 |
| Molecular sieve 5A[3] | 20.00 |  |  |
| Zeolite A (activated)[4] |  | 20.00 | 20.00 |
| Silica aerogel[5] | 5.00 | 5.50 | 5.50 |
| Titanium dioxide | 0.40 | 0.40 | 0.40 |
| Flavor | 0.65 | 1.00 | 1.00 |
| Sodium saccharine | 0.20 | 0.10 | 0.10 |
| Sodium lauryl sulfate | 1.20 | 1.20 | 1.30 |
| FD & C Blue #1 |  | 0.10 |  |
| (1% in glycerine) |  |  |  |

[1]Available from Union Carbide as Carbowax 600.
[2]Available from Kelco Division of Merck as Gelrite.
[3]Anhydrous zeolite available from Linde Division of Union Carbide.
[4]Available from P.Q. Corporation as Valfor NaHA; produced in accordance with U.S. Pat. No. 4,349,533.
[5]Available from Davison Division of Grace Inc. as Syloid 244.

The dentifrices have a brittle gel vehicle. They are introduced into dentifrice tubes and are extruded therefrom as ribbons which readily and cleanly separate from dentifrice still in the tubes when extrusion pressure is released. When moistened in the oral cavity, heat is generated in each dentifrice which is sensed by the user during toothbrushing. The heat evolved is not sufficient to reverse the gels formed by S-60 and glycerine.

EXAMPLE 3

The following stable anhydrous dentifrice is prepared by hot processing at 85° C.

|  | PARTS |
|---|---|
| Glycerine (99.3%) | 70.35 |
| Polyethylene glycol 600[1] | 3.00 |
| Clarified deacetylated heteropolysaccharide S-60[2] | 0.40 |
| Silica containing combined 1% alumina[3] | 18.00 |
| Silica aerogel[4] | 5.50 |
| Titanium dioxide | 0.40 |
| Flavor | 0.65 |
| Aspartame | 0.50 |
| Sodium lauryl sulfate | 1.20 |

[1]Available from Union Carbide as Carbowax 600.
[2]Available from Kelco Division of Merck as Gelrite.
[3]Available from J.M. Huber as Zeo 49B.
[4]Available from Davison Division of Grace Inc. as Syloid 244.

EXAMPLE 4

The following stable anhydrous (A) and heat-generating and effervescent (B) dentifrices are prepared by hot processing at 85° C.

|  | PARTS | |
|---|---|---|
|  | A | B |
| Glycerine (99.3%) | 68.30 | 63.15 |
| Polyethylene glycol 600[1] | 3.00 | 3.00 |
| Clarified deacetylated heteropolysaccharide S-60[2] | 0.40 | 0.40 |
| Sodium bicarbonate | 20.00 | 3.75 |
| Zeolite A[3] |  | 20.00 |
| Silica aerogel[4] | 5.50 | 5.50 |
| Monosodium phosphate |  | 1.00 |
| Titanium dioxide | 0.40 | 0.40 |
| Flavor | 1.00 | 1.00 |
| Sodium saccharin | 0.20 | 0.30 |
| Sodium lauryl sulfate | 1.20 | 1.50 |

[1]Available from Union Carbide as Carbowax 600.
[2]Available from Kelco Division of Merck as Gelrite.
[3]Available from P.Q. Corporation as Valfor NaHA; produced in accordance with U.S. Pat. No. 4,349,533.
[4]Available from Davison Division of Grace Inc. as Syloid 244.

EXAMPLE 5

The following stable anhydrous dentifrice with water soluble calcium and fluoride ions is prepared by hot processing at 85° C.

|  | PARTS |
| --- | --- |
| Glycerine 99.3% | 72.815 |
| Non-clarified deacetylated heteropolysaccharide S-60[1] | 0.500 |
| Silica containing combined 1% alumina[2] | 18.000 |
| Silica Aerogel[3] | 5.000 |
| Calcium Chloride | 0.125 |
| Sodium monofluorophosphate | 0.760 |
| Titanium dioxide | 0.500 |
| Flavor | 0.650 |
| Sodium saccharin | 0.200 |
| Sodium lauryl sulfate | 1.200 |

[1] Available from Kelco Division of Merck as Gellan Gum.
[2] Available from J.M. Huber as Zeo 49B.
[3] Available from Davison Division of Grace, Inc.

What is claimed is:

1. An anhydrous dentifrice comprising at least about 50% by weight of glycerine humectant, at least 0.1% by weight of deacetylated heteropolysaccharide S-60 to provide a rigid gel consistency to said dentifrice, about 5-50% by weight of dentally acceptable polishing agent selected from the group consisting of anhydrous zeolite, sodium bicarbonate, alpha-alumina hydrate, calcium sulfate, aluminum silicate, dicalcium phosphate, tricalcium phosphate, insoluble sodium metaphosphate, silica xerogen, sodium aluminasilicate, magnesium carbonate, calcium carbonate, calcium pyrophosphate and bentonite and said anhydrous dentifrice further contains a fluoride-providing compound in amount which provides about 0.01-1% by weight of water-soluble fluoride content to said anhydrous dentifrice upon contact with water or saliva, said fluoride-providing compound being selected from the group consisting of sodium fluoride, stannous fluoride, manganese fluoride, potassium fluoride, potassium stannous fluoride, sodium hexafluorostannate, stannous chlorofluoride, sodium fluorozirconate, potassium fluorozirconates and sodium monofluorophosphate.

2. The anhydrous dentifrice claimed in claim 1 wherein said polishing material includes sodium aluminosilicate.

3. The anhydrous dentifrice claimed in claim 1 wherein said fluoride-providing compound is selected from the group consisting of sodium fluoride, stannous fluoride and sodium monofluorophosphate.

4. The anhydrous dentifrice claimed in claim 3 wherein said fluoride-providing compound is sodium monofluorophosphate.

5. The anhydrous dentifrice claimed in claim 1 wherein said polishing agent includes anhydrous zeolite in amount of about 1-50% by weight of said dentifrice.

6. The anhydrous dentifrice claimed in claim 1 wherein said polishing material includes about 20% by weight of anhydrous zeolite and about 3.75% by weight of sodium bicarbonate.

* * * * *